United States Patent [19]

Trick

[11] Patent Number: 4,852,555
[45] Date of Patent: Aug. 1, 1989

[54] INFLATABLE PENILE PROSTHESIS

[75] Inventor: Robert E. Trick, Racine, Wis.

[73] Assignee: Medical Engineering Corporation, Racine, Wis.

[21] Appl. No.: 128,016

[22] Filed: Dec. 2, 1987

[51] Int. Cl.⁴ .............................................. A61F 2/26
[52] U.S. Cl. .................................................. 128/79
[58] Field of Search ...................................... 128/79

[56] References Cited

U.S. PATENT DOCUMENTS

| 4,267,829 | 5/1981 | Burton et al. | 128/79 |
| 4,378,792 | 4/1983 | Finney | 128/79 |
| 4,682,589 | 7/1987 | Finney | 128/79 |

FOREIGN PATENT DOCUMENTS

| 0000302 | 3/1980 | PCT Int'l Appl. | 128/79 |
| 2163655 | 3/1986 | United Kingdom | 128/79 |

Primary Examiner—Robert P. Swiatek
Assistant Examiner—Cary E. Stone
Attorney, Agent, or Firm—Stuart E. Krieger

[57] ABSTRACT

A penile prosthesis is disclosed that can be extended and retracted by the application of fluid pressure to an internal chamber. The chamber includes a non-dispensible sheath portion that can be reversibly extended from a wrinkled retracted condition to a taut extended condition in response to the amount of fluid pressure in the internal chamber.

5 Claims, 1 Drawing Sheet

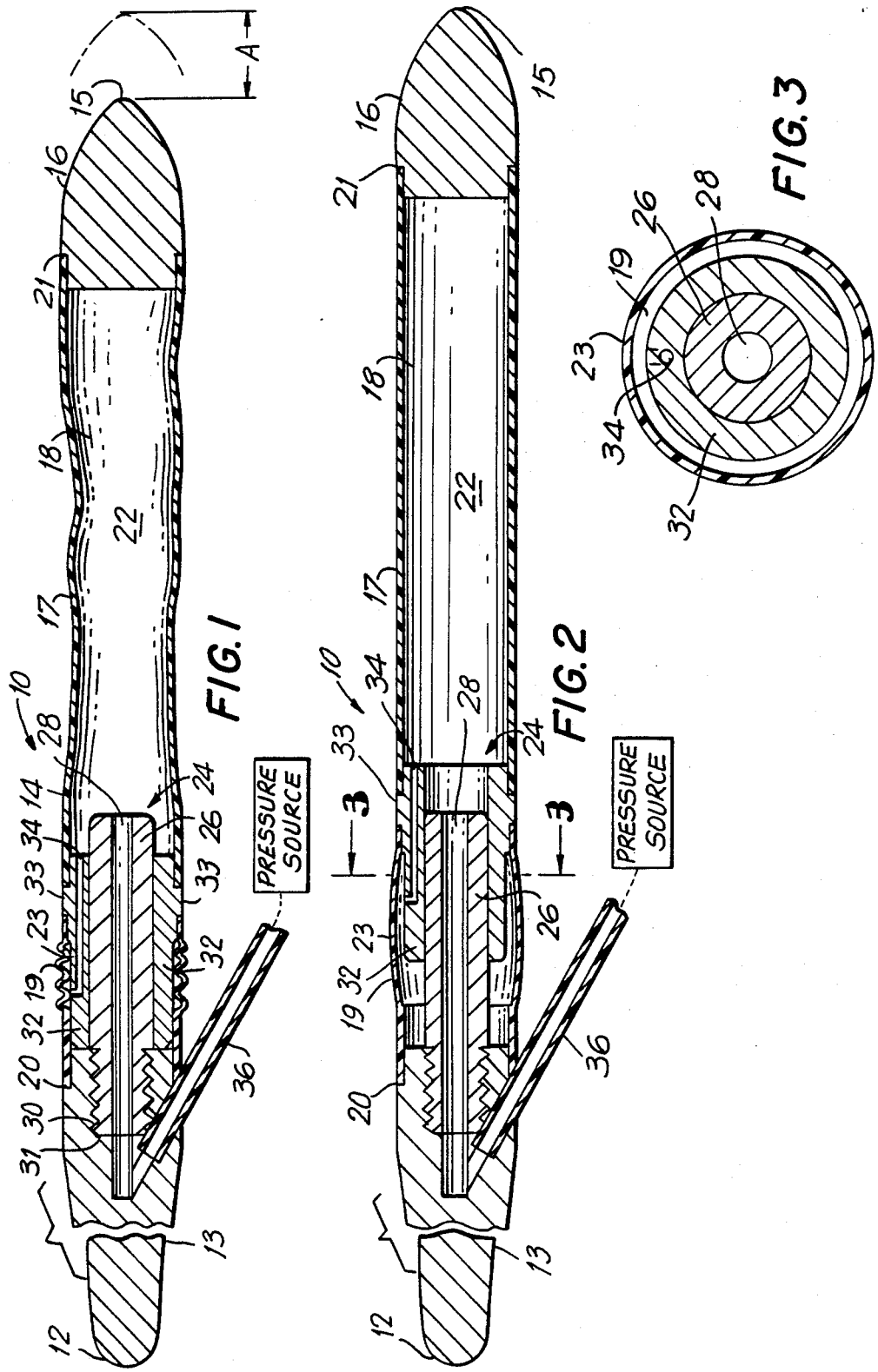

INFLATABLE PENILE PROSTHESIS

FIELD OF THE INVENTION invention relates to penile prostheses for curing erectile impotence and more particularly, it relates to the longitudinal extension and retraction of an inflatable penile prosthesis.

BACKGROUND OF THE INVENTION

Surgical implantation of penile prostheses is a known practical means of remedying male impotency. Several types of penile prostheses are known in the art. One type includes a pair of biocompatible rods having a predetermined stiffness. The rods are solid and composed of silicone rubber and each rod is implanted into a corpus cavernosum of the penis. The rods are not extensible and have a stiffness that is not variable.

Another type of known prosthesis is referred to as an inflatable penile prosthesis. An example of this type is described in U.S. Pat. No. 3,954,102 to Buuck. This prosthesis includes two elongated inflatable distensible cylinders that are surgically implanted within the corpus cavernosa of the penis. The two cylinders are connected by a tubing to a pressure source that is implanted elsewhere in the body. The pressure source pumps fluid into the prosthesis for the purpose of producing inflation. The distensible cylinders are collapsible so that they can be easily implanted. The distensibility is provided by the stretching of the material encompassing the inflatable chamber.

Some physicians and patients consider it desirable to implant a prosthesis that can be increased in length when the device is transformed from the flaccid state to the stiff erect state. It is desirable to obtain this result in a manner that provides reliability and does not undesirably fatigue the material used.

Accordingly, it is desirable to have an inflatable penile prosthesis in which the length of the prosthesis can be easily and reliably extended and retracted.

It is accordingly the general object of the present invention to disclose an improved inflatable penile prosthesis with means for increasing its length when transformed from the flaccid state to the erect state.

It is a further object to disclose a penile prosthesis which does not require stretching or shortening of distensible material to achieve extension and retraction, respectively.

It is an additional object to disclose a penile implant in which the penile length can be adjusted.

SUMMARY OF THE INVENTION

In accordance with these and other objects there is provided by the present invention a penile prosthesis which includes an elongated cylindrical body having a distal tip portion, proximal stem portion, and an intermediate portion therebetween. The intermediate portion includes an inflatable chamber that can be pressurized by fluid. A flexible sheath surrounds the chamber, which includes a flexible, non-distensible portion that can be adjustably and repeatedly varied in its elongation between a wrinkled fully retracted condition and a relatively taut and extended condition. A pressure source is interconnected to the inflation chamber. By controlling the amount of fluid pressure applied by the pressure source to the chamber the amount of extension or retraction of the distensible portion can be controlled. In the extended state the penile prosthesis is erect and in the retracted state the prosthesis is flaccid.

BRIEF DESCRIPTION OF THE DRAWINGS

FIG. 1 is a cross-sectional view of an inflatable penile prosthesis in accordance with the present invention in a retracted or non-erect condition; and FIG. 2 is a cross-sectional view of the penile prosthesis of FIG. 1 in an extended or erect condition.

FIG. 3 is a transverse cross-sectional view of the penile prosthesis taken along line 3—3 of FIG. 2.

DESCRIPTION OF THE PREFERRED EMBODIMENT

The preferred embodiment of the penile erectile system of the present invention comprises a pair of elongated penile prostheses that are identical, therefore, only one will be described in detail.

Referring now to FIG. 1-3, the penile prosthesis in accordance with the present invention, generally designated by the numeral 10, has a proximal tip 12, intermediate cylindrical portion 14, and a distal tip 15. The external portion of the prosthesis 10 is composed of a biocompatible material, preferably a silicone elastomer.

The proximal tip 12 is at the end of a stem portion 13. The stem portion 13 is composed of a relatively stiff material and is implanted in the root end of the corpus cavernosum of the penis. The distal tip 15 is at the end of the distal tip portion 16. The intermediate cylindrical portion 14 and distal tip portion 16 are relatively flexible and are implanted in the portion of the corpus cavernosum in the pendulous penis (not shown). Each of the implants is implanted in a separate corpus cavernosum of the penis.

The intermediate cylindrical portion 14 includes an outer sheath 17 which surrounds an inner fluid receiving chamber 18 that includes an expansion space 19. The sheath 17 which forms the outer wall of the fluid receiving chamber 18 is preferably composed of a relatively inelastic material, such as silicone coated mesh or woven fabric, so that the sheath is non-distensible even when pressurized. Alternatively, the sleeve may be composed of a distensible material such as nonreinforced silicone rubber. The necessary fluid tight seal between the sheath 17 and the intermediate portion 14 occurs at 20 and the seal between the sheath 17 and the distal tip portion 16 occurs at 21. The seals may be made with a suitable adhesive or other means.

In the non-pressurized state the chamber 18 is filled with a non-compressible fluid 22 which may be of a biocompatible fluid. Possible fluids include saline or a free flowing silicone gel. In the non-pressurized state, the soft flexible intermediate cylindrical portion 14 of the prosthesis 10 flexes and permits the penis to assume a substantially normal flaccid condition, as shown in FIG. 1.

When the prosthesis 10 is pressurized as shown in FIG. 2, the intermediate cylindrical portion 14 becomes rigid as a result of the pressurization of the chamber 18 and the penis assumes an erect condition.

The intermediate portion 14 includes a chamber 18 for receiving fluid and means for extending the penile prosthesis 10. The extending means includes a sheath portion 23 and a mount means generally designated by the numeral 24. The sheath portion 23 has a fully wrinkled-retracted condition as shown in FIG. 1 which occurs when the prosthesis 10 is non-pressurized, and a taut and fully extended condition as shown in FIG. 2 when the prosthesis 10 is fully pressurized. The fully extended length (shown in phantom FIG. 1) is longer than the fully retracted length by the distance A.

The mount means includes a pin 26, preferably composed of stainless steel, having a central bore 28 and outside threads 30. The pin 26 is centrally secured to the intermediate portion 14 by threading it into the pre-threaded hole 31. The pin 26 may be otherwise secured by adhesive. A moveable cylinder 32 is mounted about the pin 26 so as to slide proximally and distally along the pin 26. The cylinder 32 has an outer surface 33 secured to the proximate end of the sheath portion 23.

The moveable cylinder 32 has an internal passageway 34 that interconnects the inflation chamber 18 with the expansion space 19.

During inflation of the prosthesis 10 the pressurized fluid 22 is provided by the pressure source via tubing 36 and the central bore 28 into the inflation chamber 18 and subsequently into the expansion space 19.

The fluid 22 is added to the penile prosthesis 10 by the pressure source. The fluid 22 flows sequentially through the tubing 36, central bore 28 and into the inflation chamber 18. From the inflation chamber 18 it flows through the interconnecting internal passageway 34 and into the expansion space 19. This increase in fluid 22 and fluid pressure in the expansion space 19 causes the moveable cylinder 32 to slide along the pin 26 distally. Distal movement of the moveable cylinder 32 and attached sheath portion 23 causes the wrinkled and retracted sheath portion 23 (FIG. 1) to move distally and become taut and extended (FIG. 2). This causes elongation of the prosthesis 10 by the distance A.

When the fluid is withdrawn by the pressure source from the elongated prosthesis 10, the moveable cylinder slides proximally along the pin 26. This causes the attached sheath portion 23 to move proximally and change from the taut and extended condition (FIG. 2) to a wrinkled and retracted condition (FIG. 1).

By controlling the amount of fluid flow (fluid pressure) with the pressure source, the prosthesis 10 can be selectively varied in length to any gradation between the fully extended condition (FIG. 2) and the fully retracted condition (FIG. 1).

I claim:

1. A penile prosthesis comprising
an elongated cylindrical body having a proximal tip at one end, a distal tip at the other end, and an intermediate portion therebetween,
said intermediate portion having a fluid pressurizable internal chamber, an anchoring stem at one end of the internal chamber, a flexible cylindrical sheath surrounding said chamber, said sheath including a flexible substantially non-distensible portion, said portion being adjustable lengthwise from a wrinkled retracted state to a relatively taut and extended state in response to a change of fluid pressure in said chamber, said sheath portion being fixedly secured to said anchoring stem, said intermediate portion further including a moveable mount within said internal chamber secured to said sheath portion, said moveable mount being reversibly moveable proximally and distally, said sheath portion being in a retracted state when said moveable mount is proximal and in an extended state when said moveable mount is distal, fixed support means within said intermediate portion for supporting said moveable mount, said moveable mount being slideable along said fixed support means, said sheath portion being secured to said moveable mount, and
varying means for varying the fluid pressure within said chamber.

2. The penile prosthesis of claim 1, wherein said fixed support means is secured to said stem.

3. The penile prosthesis of claim 2, said fixed support means including a pin, said pin having a passage therethrough, said passage being in fluid communication with said inflation chamber.

4. The penile prosthesis of claim 1, said varying means including adjusting means for reversibly adjusting the pressure in said inflation chamber between a low pressurized state and a more pressurized state.

5. A method of controlling the length of an inflatable penile prosthesis comprising the steps of
providing an elongated cylindrical hollow penile prosthesis having an internal fluid pressurizable chamber, a flexible sheath surrounding said chamber,
securing a moveable mount within said chamber to said sheath, said sheath being retractable or extendible,
securing a fixed support within said chamber,
moving said mount along said fixed support, said mount moving to retract said sheath when said internal fluid pressure is low and said mount moving to extend said sheath when said internal fluid pressure is high, and
adjusting said fluid pressure within said chamber between low and high for moving said mount.

* * * * *